United States Patent
Sidot et al.

(10) Patent No.: US 8,846,921 B2
(45) Date of Patent: Sep. 30, 2014

(54) METHOD FOR PRODUCING 3,7-DIAZA-BICYCLO[3.3.1]NONANE METAL COMPLEXES

(75) Inventors: Christian Sidot, Compiegne (FR); Audrey Caron, Compiegne (FR); Miriam Ladwig, Diezenbach (DE); Gerd Reinhardt, Kelkheim (DE)

(73) Assignee: Clariant Finance (Bvt) Ltd, Tortola (VG)

( * ) Notice: Subject to any disclaimer, the term of this patent is extended or adjusted under 35 U.S.C. 154(b) by 0 days.

(21) Appl. No.: 13/877,567

(22) PCT Filed: Oct. 6, 2011

(86) PCT No.: PCT/EP2011/004982
§ 371 (c)(1),
(2), (4) Date: May 9, 2013

(87) PCT Pub. No.: WO2012/048815
PCT Pub. Date: Apr. 19, 2012

(65) Prior Publication Data
US 2014/0114073 A1    Apr. 24, 2014

(30) Foreign Application Priority Data

Oct. 11, 2010 (EP) .................................. 10290547

(51) Int. Cl.
*C07F 15/02* (2006.01)
*C07F 13/00* (2006.01)

(52) U.S. Cl.
CPC .............. *C07F 15/02* (2013.01); *C07F 13/005* (2013.01); *C07F 13/00* (2013.01); *C07F 15/025* (2013.01)
USPC ......................................................... 546/10

(58) Field of Classification Search
None
See application file for complete search history.

(56) References Cited

U.S. PATENT DOCUMENTS

2011/0263857 A1 * 10/2011 Sajitz et al. ..................... 546/10

* cited by examiner

*Primary Examiner* — Janet L Andres
*Assistant Examiner* — Timothy R Rozof
(74) *Attorney, Agent, or Firm* — Michael W. Fonell

(57) ABSTRACT

The invention relates to a method for producing metal complexes of formula (2) $[M_aL_xX_n]Y_m$ (2), where M is a metal from the group consisting of Mn(II), Mn(III), Mn(IV), Fe(II), Fe(III) or Fe(IV), X is a coordinating compound selected from mono-, bi- or tri-charged anions or neutral molecules which can coordinate to a metal in mono-, bi- or tri-dentate form, Y represents a non-coordinating counter-ion which ensures charge equalization of the complex, L represents a ligand of formula (1) or the protonized or de-protonized form thereof, and a, x, n, m, R, $R^1$, $R^2$, $R^3$ and z have the meanings described in claim 1. Said method is characterized in that the reaction of one or more ligands of formula (1) with an iron salt or manganese salt is carried out in an acetone/water mixture in a temperature range from 0 to 50° C. and for this purpose a solution or a suspension of the one or more ligands of formula (1) in acetone is brought in contact with an aqueous metal salt solution of the iron salt or manganese salt in the temperature range in which the reaction takes place.

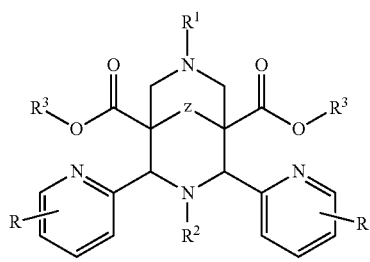

(1)

17 Claims, No Drawings

METHOD FOR PRODUCING 3,7-DIAZA-BICYCLO[3.3.1]NONANE METAL COMPLEXES

The invention relates to a process for preparing iron or manganese complexes with 3,7-diazabicyclo[3.3.1]nonane ligands.

3,7-Diazabicyclo[3.3.1]nonane compounds are compounds of interest for various applications. Among other things, transition metal complexes containing a ligand of the formula (1)

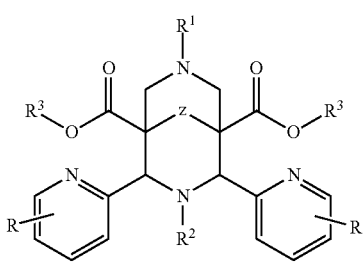

are very effective catalysts which can be used in combination with peroxides for bleaching of colored stains in washing and cleaning compositions. Examples thereof can be found in WO 00/60045 and EP 1 678 286. For this application, high product purities are required, since traces of free metal ions can contribute to unwanted side reactions and hence to damage to the laundry. Some of these complexes, however, are also very active in the presence of atmospheric oxygen and enable bleaching of oily stains without using the otherwise customary hydrogen peroxides or inorganic per salts. Examples thereof are described, inter alia, in WO 03/104234.

Due to their mechanism of action with oxygen, a further field of use for this substance class has opened up in recent times. For instance, WO 2008/003652 describes the use of such transition metal complexes as catalysts for the drying of alkyd-based paints and coatings. They serve here as an environmentally friendly alternative to cobalt-containing fatty acid derivatives which are suspected of causing cancer.

Ligands of the formula (1) and metal complexes thereof have been described in detail in the literature. Ligand synthesis is described, for example, in Arzneimittelforschung 1965, 15(11), 1327-1330, in Eur. J. Org. Chem. (2008) 1019-1030 or in WO 2006/133869, while WO 00/60045, WO 02/488301 and Inorg. Chimica Acta, 337 (2002) 407-419 describe complexation reactions.

The known complex syntheses are effected by reaction of the respective ligand of the formula (1) with a metal salt in homogeneous or heterogeneous solution. In most cases, operation is effected under anhydrous conditions in an organic solvent. Both the ligand and the metal salt are dissolved separately in organic solvents such as acetonitrile or methanol, and then the complex formation is conducted in homogeneous solution. Operation is effected here under argon or nitrogen under anhydrous conditions. Since the metal complexes formed also have good solubility in the solvent mixture, a further solvent (usually ether) has to be used for isolation of the complexes, in order to be able to isolate the product in crystalline form. Frequently, the complex then has to be recrystallized for further purification. The yields are only moderate and are between 40 and 70%.

The synthesis processes described require, for the isolation of the end product, at least two different organic solvents and strictly anhydrous conditions (anhydrous solvents, argon or nitrogen blanketing of the reaction), as a result of which the industrial scale implementation of the reaction causes problems and expense.

Under particular conditions, the complexation reaction can also be performed as a heterogeneous reaction in water, as described, for example, in WO 2010/069524. In this case, an aqueous solution of an iron(II) salt is added to a suspension of the ligand in water, and, after a certain reaction time, the iron(II) complex of the ligand (1) is isolated either by spray drying or by filtration and drying. This process affords good yields, but the purity of the complex is only in the order of magnitude of 95%. This is not astonishing, since by-products such as iron(III) ions, which are always present in iron(II) salts, and unconverted ligand, cannot be removed in the spray drying. This is also true of isolation by filtration, since the uncomplexed ligand is insoluble in water and remains in the end product. In this mode of operation too, it is possible only with very great difficulty to remove adhering residual amounts of iron(III) salts, since the iron(II) complex of the ligand of the formula (1) has a water solubility of 7% by weight, and the isolated yield is lowered in the case of excessive frequency of washing.

It is thus an object of the present invention to provide an improved process performable on the industrial scale for preparation of metal complexes with ligands of the formula (1), the metal complexes being obtainable especially with high purities.

It has now been found that, surprisingly, this object is achieved and iron and manganese complexes of the formula (2) below can be prepared in high purities when working in an acetone/water solvent mixture.

The present invention therefore provides a process for preparing one or more metal complexes of the formula (2)

$$[M_aL_xX_n]Y_m \quad (2)$$

where
M is a metal from the group of Mn(II), Mn(III), Mn(IV), Fe(II), Fe(III) and Fe(IV),
X is a coordinating compound selected from singly, doubly and triply charged anions and uncharged molecules capable of mono-, bi- or tridentate coordination to a metal, preferably $OH^-$, $NO_3^-$, $NO$, $S^{2-}$, $R^aS^-$, $PO_4^{3-}$, $H_2O$, $CO_3^{2-}$, $R^bOH$, $Cl^-$, $Br^-$, $CN^-$, $ClO_4^-$, $R^aCOO^-$ or $SO_4^{2-}$, where $R^a$ is H or $C_1$-$C_4$ alkyl and $R^b$ is $C_1$-$C_4$ alkyl,
Y is a noncoordinating counterion which ensures the charge balance of the complex, preferably $R^cSO_4^-$, $SO_4^{2-}$, $NO_3^-$, $Cl^-$, $Br^-$, $I^-$, $ClO_4^-$, $BF_4^-$, $PF_6^-$ or $R^cSO_3^-$, where $R^c$ is H or $C_1$-$C_4$ alkyl,
a is 1 or 2 and preferably 1,
x is 1 or 2 and preferably 1,
n is a number from 0 to 4,
m is a number from 0 to 8, and
L is a ligand of the formula (1) or the protonated or deprotonated form thereof

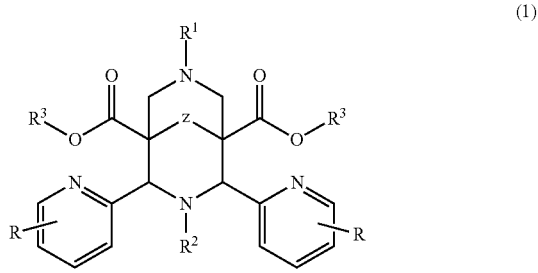

where
R is hydrogen, hydroxyl or $C_1$-$C_4$ alkyl;
$R^1$ is $C_1$-$C_4$ alkyl, $C_6$-$C_{10}$ aryl, pyridinyl-$C_1$-$C_4$-alkyl or $(CH_2)_kN(C_1$-$C_4$-alkyl$)_2$;
$R^2$ is $C_1$-$C_{20}$ alkyl, $C_6$-$C_{10}$ aryl or pyridinyl-$C_1$-$C_4$-alkyl;
$R^3$ is $C_1$-$C_4$ alkyl;
z is C=O or C(OH)$_2$ and
k is a number from 1 to 6,
wherein the reaction of one or more ligands of the formula (1) with an iron or manganese salt, especially iron(II) chloride, takes place in an acetone/water mixture within the temperature range from 0 to 50° C., preferably 5 to 35° C. and more preferably 10 to 25° C., and for this purpose a solution or suspension, preferably a solution, of the one or more ligands of the formula (1) in acetone is contacted with an aqueous metal salt solution of the iron or manganese salt within the temperature range in which the reaction takes place.

The ligands of the formula (1) are of good solubility in acetone. The metal complexes of the formula (2) are of poor solubility in acetone/water mixtures. In the case of addition of the aqueous solution of the metal salt to the solution of the ligand of the formula (1) in acetone, or vice versa, there is an immediate complexation reaction from which the corresponding metal complex of the formula (2) precipitates. Since both unconverted ligand of the formula (1) and any unconverted metal salt are of good solubility in acetone/water, they can be readily removed therefrom after isolation of the metal complex of the formula (2). Thus, the desired metal complexes of the formula (2) are obtained in high purities and in good space-time yields.

The metal complexes of the formula (2) prepared by the process according to the invention preferably have purities of >99% (determination by HPLC).

Particular preference is given to preparing, by the process according to the invention, one or more complexes of the formula [FeLCl]Cl, [FeL(SO$_4$)], [MnLCl]Cl, [MnL(SO$_4$)], [FeLCl]PF$_6$, [FeL(H$_2$O)][PF$_6$]$_2$ or [FeL(H$_2$O)][BF$_4$]$_2$, where L is especially selected from the group consisting of
dimethyl 2,4-di(2-pyridyl)-3-methyl-7-(pyridin-2-ylmethyl)-3,7-diazabicyclo-[3.3.1]nonan-9-one-1,5-dicarboxylate (N2Py3o),
dimethyl 2,4-di(2-pyridyl)3-(pyridin-2-ylmethyl)-7-methyl-3,7-diazabicyclo-[3.3.1]nonan-9-one-1,5-dicarboxylate (N2Py3u),
diethyl 2,4-di(2-pyridyl)-3-methyl-7-(pyridin-2-ylmethyl)-3,7-diazabicyclo-[3.3.1]nonan-9-one-1,5-dicarboxylate,
dimethyl 2,4-di(2-pyridyl)-3,7-bis(pyridin-2-ylmethyl)-3,7-diazabicyclo[3.3.1]-nonan-9-one-1,5-dicarboxylate (N2Py4),
dimethyl 2,4-di(2-pyridyl)-3,7-dimethyl-3,7-diazabicyclo [3.3.1]nonan-9-one-1,5-dicarboxylate (N2Py2),
diethyl 2,4-di(2-pyridyl)-3,7-dimethyl-3,7-diazabicyclo [3.3.1]nonan-9-one-1,5-dicarboxylate,
dimethyl 2,4-di(2-pyridyl)-3-methyl-7-(N,N'-dimethylethylamine)-3,7-diazabicyclo[3.3.1]nonan-9-one-1,5-dicarboxylate
and the corresponding dihydroxy ketals.

In an embodiment of the invention which is preferred in turn, the process according to the invention is used to prepare one or more complexes of the formula [FeLC]Cl, [FeL(SO$_4$)], [MnLCl]Cl or [MnL(SO$_4$)], more preferably one or more complexes of the formula [FeLCl]Cl or [FeL(SO$_4$)] and especially preferably one or more complexes of the formula [FeLCl]Cl.

Ligands of the formula (1) used in the process according to the invention are complexed by the process and are thus found in the metal complexes of the formula (2) prepared. However, they can be modified in the metal complexes of the formula (2) in such a way that a ketone or carbonyl group z (z=C=O) present in the starting ligands of the formula (1) is converted to the hydrated form (z=C(OH)$_2$) during the process according to the invention by the presence of water. This means that the ligands in the metal complexes of the formula (2) may be present as dihydroxy ketals even if they have been used in the form of the ketones in the process according to the invention.

The fact that the ligands are often present in complexed form as dihydroxy ketals (z=C(OH)$_2$) is shown, for example, in Inorg. Chimica Acta, 337 (2002) 407-419 by X-ray structure analysis.

The ligands can be prepared on the industrial scale according to the information in DE 601 20 781 or WO 2006/133869 as per the following reaction scheme:

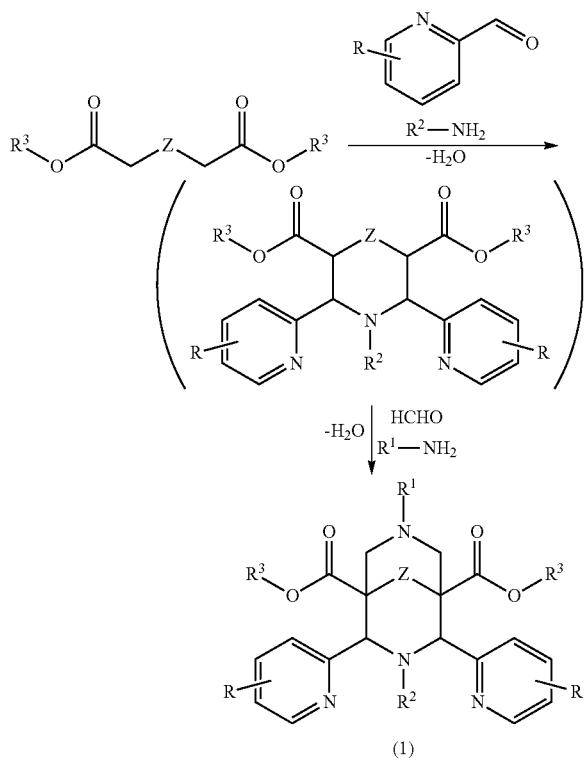

Proceeding from dicarboxylic diester, two Mannich condensation steps with elimination of water are conducted in a $C_1$-$C_4$ alcohol, for example ethanol, propanols or butanols. After removal of water has ended, the mixture is cooled and the product is filtered off and washed. According to the preparation, the ligands may be obtained in the form of crystals of greater or lesser size. For the complexation reaction, they can then be used either in solvent-moist form or in dried form.

In a further preferred embodiment of the process according to the invention, the ligands of the formula (1) are selected from the group consisting of dimethyl 2,4-di(2-pyridyl)-3-methyl-7-(pyridin-2-ylmethyl)-3,7-diazabicyclo[3.3.1] nonan-9-one-1,5-dicarboxylate (N2Py3o), dimethyl 2,4-di(2-pyridyl)-3,7-dimethyl-3,7-diazabicyclo[3.3.1]nonan-9-one-1,5-dicarboxylate (N2Py2) and the corresponding dihydroxy ketals.

Coordinating compounds X of the metal complexes of the general formula (2) originate preferably from the iron or manganese salt used in the process according to the invention.

However, they may also originate, for example, from the solvent, especially when X=$H_2O$.

Special preference is given to coordinating compounds X selected from the group consisting of $Cl^-$ and $SO_4^{2-}$. Preference is given among these to $Cl^-$.

Noncoordinating counterions Y can also preferably originate from the iron or manganese salt used in the process according to the invention, for example when Y has the same definition as X.

Special preference is given to noncoordinating counterions Y selected from the group consisting of $Cl^-$ and $SO_4^{2-}$. Preference is given among these to $Cl^-$.

In a preferred embodiment of the invention, X and Y have the same definition.

The iron or manganese salt used in the process according to the invention is also referred to hereinafter as "metal salt" for short.

The metal salt used for the process according to the invention is preferably a metal(II) salt. In a preferred embodiment of this aspect of the invention, the metal(II) salt is an iron(II) salt, particular preference being given to iron(II) chloride and iron(II) sulfate. In a further preferred embodiment of this aspect of the invention, the metal(II) salt is selected from the group consisting of iron(II) chloride, iron(II) sulfate, manganese(II) chloride and manganese(II) sulfate. An especially preferred metal salt is iron(II) chloride.

In a particularly preferred embodiment of the process according to the invention, one or more complexes of the formula [FeLC]Cl are prepared in which L is dimethyl 2,4-di(2-pyridyl)-3-methyl-7-(pyridin-2-ylmethyl)-3,7-diazabicyclo[3.3.1]nonan-9-one-1,5-dicarboxylate (N2Py3o) or the corresponding dihydroxy ketal. In this case, dimethyl 2,4-di(2-pyridyl)-3-methyl-7(pyridin-2-ylmethyl)-3,7-diazabicyclo[3.3.1]-nonan-9-one-1,5-dicarboxylate or the corresponding dihydroxy ketal, or mixtures thereof, are reacted with with iron(II) chloride.

In a further preferred embodiment of the process according to the invention, the ligands L are used in the process in the form of the ketones (z=C=O).

In a further preferred embodiment of the process according to the invention, one or more metal complexes of the formula (2) are prepared in which the complexed ligands L are present in the form of the dihydroxy ketals (z=C(OH)$_2$).

The process according to the invention quite generally involves dissolving or suspending the one or more ligands of the formula (1) in acetone, and contacting and reacting them with an aqueous metal salt solution at the temperatures specified. Advantageously, this is done while stirring the reaction mixture.

The process according to the invention is preferably effected by dissolving or suspending the one or more ligands of the formula (1) in acetone and adding the aqueous metal salt solution of the iron or manganese salt while stirring.

The ligands of the formula (1) can be used in the process according to the invention in dried or isolated form. The ligands of the formula (1) may, however, also be used in the process according to the invention in solvent-free form without, or without complete, drying, after they have been prepared and removed from the reaction mixture, for example after they have been prepared and removed by filtration, and optionally after washing. In this case, the ligands of the formula (1) are used in the process according to the invention together with solvent. The corresponding solvent is then present preferably in an amount of <30% by weight and more preferably in an amount of <20% by weight, based in each case on the amount of ligands of the formula (1). The solvent, which in this case is introduced into the process according to the invention together with the ligands of the formula (1), is preferably a mixture of water and organic solvent and more preferably a water/alcohol mixture. The alcohol is preferably selected from $C_1$-$C_4$-alcohols and is especially preferably isobutanol.

In the process according to the invention, the weight ratio of acetone:ligand of the formula (1) is preferably from 15.0:1.0 to 0.5:1.0 and more preferably from 10.0:1.0 to 1.2:1.0. The amount of acetone required should be matched to the solubility of the ligand of the formula (1) in acetone, and may therefore vary according to the ligand of the formula (1).

In the process according to the invention, the molar ratio of ligand of the formula (1):metal salt is preferably from 0.9:1.0 to 1.2:1.0. Particular preference is given to using 0.99 to 1.01 mol of metal salt per 1 mol of ligand of the formula (1).

In the process according to the invention, the metal salt in aqueous solution is used preferably in a concentration of 10 to 50% by weight and more preferably in a concentration of 20 to 40% by weight.

In the case of addition of the metal salt to the one or more dissolved or suspended ligands of the formula (1), slight exothermicity occurs, and the metal complex of the formula (2) precipitates out of the solvent mixture. The reaction may be completed by continued stirring. Subsequently, the product can be isolated by filtration or centrifugation, and washed.

The metal complexes of the formula (2) can be removed in solid form from the reaction mixture by methods familiar to those skilled in the art, preferably by filtration. Preference is given to washing the metal complex of the formula (2) after removal from the reaction mixture. For washing, preference is given to using acetone, water or acetone/water mixtures. Preference is given to drying the metal complex after removal from the reaction mixture and preferably after washing.

The process according to the invention is preferably performed at temperatures of 5 to 35° C. and more preferably at temperatures of 10 to 25° C. Especially at these temperatures, crystalline metal complexes of the formula (2) with very good filtration properties and low residual moisture contents in the filtercake are obtained in high yields. After drying the metal complexes of the formula (2), a free-flowing powder is obtained, the grinding of which can be dispensed with.

The process according to the invention can be performed under protective gas atmosphere, for example under nitrogen atmosphere.

Preference is given to performing the process according to the invention under ambient pressure.

In a further preferred embodiment of the invention, X and Y have different definitions. In this case, it is possible, for example, first to prepare metal complexes of the formula (2) in which X and Y have the same definition and are more preferably chloride, and then to exchange the non-coordinating counterion Y. In this procedure, for exchange of Y, preference is given to using an alkali metal or alkaline earth metal salt containing the new noncoordinating counterion Y. For example, it is possible to obtain metal complexes of the formula (2) where Y=$PF_6^-$ (hexafluorophosphates) by first preparing metal complexes where X=Y=$Cl^-$ and then exchanging the noncoordinating $Cl^-$ counterion by means of $KPF_6$ for the new noncoordinating $PF_6^-$ counterion. Such exchange reactions are common knowledge to the person skilled in the art.

Compared to the prior art processes, good space-time yields, short filtration and drying times and high product purities are achieved in the process according to the invention.

Examples which follow are intended to illustrate the invention in detail without restricting it thereto.

EXAMPLES

Preparation of the dimethyl 2,4-di(2-pyridyl)-3-methyl-7-(pyridin-2-ylmethyl)-3,7-diazabicyclo[3.3.1] nonan-9-one-1,5-dicarboxylate ligand (N2Py3o)

11.2 kg of dimethyl acetonedicarboxylate (purity 97% by weight; 64 mol) are dissolved in 15 kg of isobutanol. The solution is cooled to 10° C., then 13.4 kg of pyridine-2-aldehyde (purity 99% by weight, 125 mol) in 10 kg of isobutanol, followed by 4.8 kg of methylamine (40% by weight in water, 62 mol), are added dropwise such that the temperature is maintained with constant cooling. The reaction mixture is then heated to 40-45° C. and an azeotrope (17 liters) of isobutanol and water is distilled off under reduced pressure at internal temperature 40-45° C. During this, 15 liters of isobutanol are metered in continuously. After cooling to room temperature, 8.4 kg of aminomethylpyridine (78 mol) are metered in and the metering funnel is rinsed with 7.0 kg of isobutanol. Then 13.5 kg of formaldehyde solution (37% by weight in water, 166.5 mol) are added within 15-30 minutes. After addition has ended, the mixture is heated to 55-60° C. and stirred for a further 1.5 hours. Subsequently, at maximum internal temperature 60° C., 55 kg of azeotropic mixture of isobutanol and water are distilled off, while 36 kg of isobutanol are added continuously. The mixture is vented with nitrogen and cooled to room temperature. The precipitate formed is filtered off and washed with isobutanol. The ligand can be used in the complexation reaction in the form of the moist filtercake, or else dried under reduced pressure at 50° C. This affords 23.3 kg (72.1%) of dimethyl 2,4-di(pyridyl)-3-methyl-7-(pyridin-2-ylmethyl)-3,7-diazabicyclo[3.3.1] nonan-9-one-1,5-dicarboxylate in the form of a colorless, crystalline powder.

Example 1

Iron (1+), chloro[dimethyl 9,9-dihydroxy-3-methyl-2,4-di(2-pyridinyl-κN)-7-[(2-pyridinyl-κN)methyl]-3,7-diazabicyclo[3.3.1]nonane-1,5-dicarboxylate-κN3, κN7]-, chloride (1:1)

186.8 kg (362.7 mol) of dimethyl 2,4-di(2-pyridyl)-3-methyl-7-(pyridin-2-ylmethyl)-3,7-diazabicyclo[3.3.1]nonan-9-one-1,5-dicarboxylate were dissolved in 1100 kg of acetone at 10-14° C. under nitrogen atmosphere. Subsequently, a 30% by weight $FeCl_2$ solution in water (154 kg; 364 mol) was added within 1 hour and the mixture was stirred at 18-22° C. for a further 4 hours. The finely crystalline yellow precipitate was filtered off within 15 minutes and washed twice with cold acetone. The product was dried at 30° C. under reduced pressure. This gave 232.5 kg of iron (1+), chloro[dimethyl 9,9-dihydroxy-3-methyl-2,4-di(2-pyridinyl-κN)-7-[(2-pyridinyl-κN)methyl]-3,7-diazabicyclo [3.3.1]nonane-1,5-dicarboxylate-κN3, κN7]-, chloride (1:1) as a yellow powder. Active content 99.9% (HPLC); yield: 94%.

Comparative Example 1

According to WO 2010/069524

A reaction vessel is charged with 220.0 kg (12.2 mol) of water and 145.1 kg (280 mol) of dimethyl 2,4-di(2-pyridyl)- 3-methyl-7-(pyridin-2-ylmethyl)-3,7-diazabicyclo[3.3.1] nonan-9-one-1,5-dicarboxylate (N2Py3o), and a homogeneous suspension is produced while stirring. Subsequently, 119.5 kg (283 mol) of aqueous iron(II) chloride solution (30.2% by weight) are added within 120 minutes. During this time, the reaction mixture is kept at 20 to 25° C. To complete the reaction, stirring is continued for 25 hours and then the solids are filtered off. Due to the poor filtration properties, a filtercake with residual moisture content 44% by weight is obtained after a filtration time of 160 minutes, and is subsequently dried in a drying cabinet at 50° C. within 125 hours in order to achieve a residual moisture content of <1% by weight. In this way, iron (1+), chloro[dimethyl 9,9-dihydroxy-3-methyl-2,4-di(2-pyridinyl-κN)-7-[(2-pyridinyl-κN) methyl]-3,7-diazabicyclo[3.3.1]nonane-1,5-dicarboxylate-κN3, κN7]-, chloride (1:1) is obtained as a yellow-brown caked solid, which has to be ground prior to further processing. Yield (telquel): 96.7%; purity: 95.4% (HPLC); yield: 92.2%.

Example 2

Manganese(II) chloride complex of methyl 3,7-dimethyl-9-oxo-2,4-di-2-pyridyl-3,7-diazabicyclo[3.3.1] nonan-1,5-dicarboxylate The methyl 3,7-dimethyl-9-oxo-2,4-di-2-pyridyl-3,7-diazabicyclo[3.3.1]-nonan-1,5-dicarboxylate ligand was prepared according to Arzneimittelforschung 1965, 15(11), 1327-1330.

5 kg (11.4 mol) of methyl 3,7-dimethyl-9-oxo-2,4-di-2-pyridyl-3,7-diazabicyclo[3.3.1]nonan-1,5-dicarboxylate were dissolved at room temperature (20° C.) in 60 kg of acetone. While stirring, 2.26 kg (11.4 mol) of manganese(II) chloride tetrahydrate, dissolved in 5.26 kg of water, were added dropwise within 30 minutes. A beige suspension formed immediately, which was stirred for a further 30 minutes. The solids were subsequently filtered off, washed with acetone and dried at 30° C. under reduced pressure. Yield: 6.21 kg (93.5%) of beige-white finely crystalline powder of the complex of the formula (2) where M=Mn, X=Y=Cl$^-$, R=H, $R^1$=$R^2$=$R^3$=$CH_3$. Purity >99% (HPLC).

Example 3

Iron (1+), chloro[dimethyl 9,9-dihydroxy-3-methyl-2,4-di(2-pyridinyl-κN)-7-[(2-pyridinyl-κN)methyl]-3,7-diazabicyclo[3.3.1]nonane-1,5-dicarboxylate-κN3, κN7]-, chloride (1:1), prepared from moist filtercake of the ligand The procedure was according to Example 1, except that the dimethyl 2,4-di(2-pyridyl)-3-methyl-7-(pyridin-2-ylmethyl)-3,7-diazabicyclo[3.3.1]nonan-9-one-1,5-dicarboxylate was not dried but used for complexation in the form of the moist filtercake (85.6% by weight of ligand, 11.5% by weight of $H_2O$, 2.9% by weight of isobutanol). Yield 92.2% iron (1+), chloro[dimethyl 9,9-dihydroxy-3-methyl-2,4-di(2-pyridinyl-κN)-7-[(2-pyridinyl-κN)methyl]-3,7-diazabicyclo [3.3.1]nonane-1,5-dicarboxylate-κN3, κN7]-, chloride (1:1) as a yellow powder. Active content 99.7% (HPLC).

The invention claimed is:
1. A process for preparing at least one metal complex of the formula (2)

$$[M_aL_xX_n]Y_m \qquad (2)$$

where
M is a metal selected from the group consisting of Mn(II), Mn(III), Mn(IV), Fe(II), Fe(III) and Fe(IV),
X is a coordinating compound selected from the group consisting of singly, doubly and triply charged anions and uncharged molecules capable of mono-, bi- or tridentate coordination to a metal,
Y is a noncoordinating counterion which ensures the charge balance of the complex,
a is 1 or 2,
x is 1 or 2,
n is a number from 0 to 4,
m is a number from 0 to 8, and
L is a ligand of the formula (1) or the protonated or deprotonated form thereof

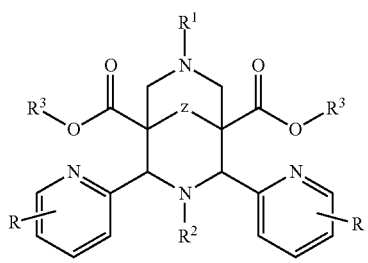

(1)

where
R is hydrogen, hydroxyl or $C_1$-$C_4$ alkyl;
$R^1$ is $C_1$-$C_4$ alkyl, $C_6$-$C_{10}$ aryl, pyridinyl-$C_1$-$C_4$-alkyl or $(CH_2)_k N(C_1$-$C_4$-alkyl$)_2$;
$R^2$ is $C_1$-$C_{20}$ alkyl, $C_6$-$C_{10}$ aryl or pyridinyl-$C_1$-$C_4$-alkyl;
$R^3$ is $C_1$-$C_4$ alkyl;
z is C=O or $C(OH)_2$ and
k is a number from 1 to 6,
comprising the steps of
(i) preparing a solution or suspension of at least one ligand of formula (1) in acetone;
(ii) preparing an aqueous metal salt solution of an iron or manganese salt;
(iii) contacting the solution or suspension of at least one ligand of formula (1) in acetone with the aqueous metal salt solution of the iron or manganese salt; and
(iv) reacting the at least one ligand of the formula (1) with the iron or manganese salt in an acetone/water mixture wherein the temperature range is from 0 to 50° C.

2. The process as claimed in claim 1, wherein X is selected from the group consisting of $OH^-$, $NO_3^-$, NO, $S^{2-}$, $R^aS^-$, $PO_4^{3-}$, $H_2O$, $CO_3^{2-}$, $R^bOH$, $Cl^-$, $Br^-$, $CN^-$, $ClO_4^-$, $R^aCOO^-$ and $SO_4^{2-}$, where $R^a$ is H or $C_1$-$C_4$ alkyl and $R^b$ is $C_1$-$C_4$ alkyl.

3. The process as claimed in claim 1, wherein Y is selected from the group consisting of $R^cSO_4^-$, $SO_4^{2-}$, $NO_3^-$, $Cl^-$, $Br^-$, $I^-$, $ClO_4^-$, $BF_4^-$, $PF_6^-$ and $R^cSO_3^-$, where $R^c$ is H or $C_1$-$C_4$ alkyl.

4. The process as claimed in claim 1, wherein the temperature range is from 5 to 35° C.

5. The process as claimed in claim 1, wherein at least one complex of the formula [FeLCl]Cl, [FeL(SO$_4$)], [MnLCl]Cl, [MnL(SO$_4$)], [FeLCl]PF$_6$, [FeL(H$_2$O)][PF$_6$]$_2$ or [FeL(H$_2$O)][BF$_4$]$_2$ is prepared, where L is selected from the group consisting of dimethyl 2,4-di(2-pyridyl)-3-methyl-7-(pyridin-2-ylmethyl)-3,7-diaza-bicyclo[3.3.1]nonan-9-one-1,5-dicarboxylate (N2Py3o),
dimethyl 2,4-di(2-pyridyl)3-(pyridin-2-ylmethyl)-7-methyl-3,7-diaza-bicyclo[3.3.1]nonan-9-one-1,5-dicarboxylate (N2Py3u),
diethyl 2,4-di(2-pyridyl)-3-methyl-7-(pyridin-2-ylmethyl)-3,7-diaza-bicyclo[3.3.1]nonan-9-one-1,5-dicarboxylate,
dimethyl 2,4-di(2-pyridyl)-3,7-bis(pyridin-2-ylmethyl)-3,7-diazabicyclo-[3.3.1]nonan-9-one-1,5-dicarboxylate (N2Py4),
dimethyl 2,4-di(2-pyridyl)-3,7-dimethyl-3,7-diazabicyclo[3.3.1]nonan-9-one-1,5-dicarboxylate (N2Py2),
diethyl 2,4-di(2-pyridyl)-3,7-dimethyl-3,7-diazabicyclo[3.3.1]nonan-9-one-1,5-dicarboxylate,
dimethyl 2,4-di(2-pyridyl)-3-methyl-7-(N,N'-dimethylethylamine)-3,7-diaza-bicyclo[3.3.1]nonan-9-one-1,5-dicarboxylate
and the corresponding dihydroxy ketals.

6. The process as claimed in claim 1, wherein the at least one ligand of the general formula (1) is selected from the group consisting of dimethyl 2,4-di(2-pyridyl)-3-methyl-7-(pyridin-2-ylmethyl)-3,7-diazabicyclo[3.3.1]nonan-9-one-1,5-dicarboxylate (N2Py3o), dimethyl 2,4-di(2-pyridyl)-3,7-dimethyl-3,7-diazabicyclo-[3.3.1]nonan-9-one-1,5-dicarboxylate (N2Py2) and the corresponding dihydroxy ketals.

7. The process as claimed in claim 2, wherein X is selected from the group consisting of $Cl^-$ and $SO_4^{2-}$.

8. The process as claimed in claim 3, wherein Y is selected from the group consisting of $Cl^-$ and $SO_4^{2-}$.

9. The process as claimed in claim 1, wherein the iron or manganese salt used is a metal(II) salt.

10. The process as claimed in claim 9, wherein the metal (II) salt is selected from the group consisting of iron(II) chloride, iron(II) sulfate, manganese(II) chloride and manganese (II) sulfate.

11. The process as claimed in claim 10, wherein the metal (II) salt is iron(II) chloride.

12. The process as claimed in claim 1, wherein at least one complex of the formula [FeLC]Cl is prepared, wherein L is dimethyl 2,4-di(2-pyridyl)-3-methyl-7-(pyridin-2-ylmethyl)-3,7-diazabicyclo[3.3.1]nonan-9-one-1,5-dicarboxylate (N2Py3o) or the corresponding dihydroxy ketal, and dimethyl 2,4-di(2-pyridyl)-3-methyl-7-(pyridin-2-ylmethyl)-3,7-diazabicyclo[3.3.1]-nonan-9-one-1,5-dicarboxylate or the corresponding dihydroxy ketal, or mixtures thereof, by the step of reacting L with iron(II) chloride.

13. The process as claimed in claim 1, wherein the weight ratio of acetone:ligand of the formula (1) is from 15.0:1.0 to 0.5:1.0.

14. The process as claimed in claim 1, wherein the molar ratio of ligand of the formula (1):metal salt is from 0.9:1.0 to 1.2:1.0.

15. The process as claimed in claim 1, wherein the metal salt in aqueous solution is used in a concentration of 10 to 50% by weight.

16. The process as claimed in claim 2, wherein Y is $Cl^-$.

17. The process as claimed in claim 3, wherein Y is $Cl^-$.

* * * * *